US005443980A

United States Patent [19]

Soberon-Chavez

[11] Patent Number: 5,443,980

[45] Date of Patent: Aug. 22, 1995

[54] **PROCESS TO OBTAIN EXTRA-CELLULAR RECOMBINANT PRODUCTS USING *XANTHOMONAS CAMPESTRIS* PV *CAMPESTRIS* AS HOST**

[75] Inventor: Gloria Soberon-Chavez, San. Cristobalcuernavaca, Mexico

[73] Assignee: Univeridad Nacional Autonoma de Mexico (UNAM), Mexico City, Mexico

[21] Appl. No.: 215,975

[22] Filed: Mar. 18, 1994

Related U.S. Application Data

[63] Continuation of Ser. No. 929,378, Aug. 14, 1992, abandoned.

[51] Int. Cl.[6] .......................... C12N 1/21; C12N 9/20; C12P 21/00

[52] U.S. Cl. .................................... 435/198; 435/69.1; 435/252.3; 435/910

[58] Field of Search ....................... 435/69.1, 104, 910, 435/198

[56] References Cited

U.S. PATENT DOCUMENTS

| | | | |
|---|---|---|---|
| 3,271,267 | 9/1966 | Weber et al. | 435/104 |
| 4,758,512 | 7/1988 | Goldberg et al. | 435/69.3 |

OTHER PUBLICATIONS

Gloria Soberon-Chavez and Beatriz Palmeros, "Pseudomonas Lipases: Molecular Genetics and Potential Industrial Applications," Critical Reviews in Microbiology 20:95–105 (1994).

A. Jeanes et al., "Polysaccharide B-1459: A New Hydrocolloid Polyelectrolyte Produced from Glucose by Bacterial Fermentation", J. Appl. Polym. Sci., 5:519–526 (1961).

E. Jansson et al., "Structure of the Extracellular polysaccharide from *Xanthomonas campestris*", Carboh. Res. 45:275–282 (1975).

M. Bagdasarian et al., "Specific-purpose plasmid cloning vectors" II. Broad host range, high copy number, RSF1010–derived vectors, and a host vector system for gene cloning in Pseudomonas, M. Bagdasarian et al, Gene 16:237–247 (1981).

"Activity of the hybrid trp–lac (tac) promoter of *Escherichia coli* in *Pseudomonas putida*. Construction of broad–host–range, controlled expression vectors," Gene 16:273–282 (1983).

Jager et al., "The effect of native and modified hyaluronate upon the formation of exolipase by *Pseudomonas aeruginosa*," FEMS Microbiol. Lett 19:59–63 (1983).

Amann et al., "Vectors bearing hybrid trp–lac promoter useful for regulated expression of cloned genes in *Escherichia coli*," Gene 25:167–178 (1983).

Daniels, et al., "Isolation of Mutants of *Xanthomonas campestris* pv. *campestris* showing Altered PatHogenicity," J. Gen. Microbiol. 130: 2447–2455 (1984).

Turner, et al., "Evidence for clustered pathogenicity genes in *Xanthomonas campestris* pv. *campestris*", Mol. Gen. Genet. 199:338–343 (1985).

Ditta et al., "Plasmids Related to the Broad Host Range Vector, pRK290, Useful for Gene Cloning and for Monitoring Gene Expression", Plasmid 13:149–153 (1985).

Stuer, et al., "Purification of Extracellular Lipase from *Pseudomonas aeruginosa*," J. Bacteriol 168:1070–1074 (1986).

Dow et al., "A Gene Cluster in *Xanthomonas Campestris* pv. *Campestris* Required for Pathogenicity Controls the Excretion of Polygalacturonate Lyase and Other Enzymes". Physiol. Mol. Plant Pathol. 31:261–271 (1987).

(List continued on next page.)

*Primary Examiner*—Charles L. Patterson, Jr.
*Assistant Examiner*—Eric Grimes
*Attorney, Agent, or Firm*—Finnegan, Henderson, Farabow, Garrett and Dunner

[57] ABSTRACT

A process using *Xanthomonas campestris* pv *capestris* to obtain desired heterologous extracellular recombinant products is provided. According to the process, the desired heterologous extracellular recombinant products can be stabilized by xanthan gum secreted into the extracellular medium.

8 Claims, No Drawings

OTHER PUBLICATIONS

Liu et al., "Cloning of Xanthomonas DNA that expresses D-xylose Catabolic Enzymes," J. Biotechnol. 6:159–1651 (1987).

Thorne, et al., "Clustering of Mutations Blocking Synthesis of Xanthum Gum by *Xanthomonas campestris*," J. Bacteriol. 169:3593–3600 (1987).

Harding et al., "Genetic and Physical Analyses of a Cluster of Genes Essential for Xanthan Gum Biosynthesis in *Xanthomonas campestris*," J. Bacteriol. 169:2854–2861 (1987).

Tang et al., "Molecular cloning of protease gene(s) from *Xanthomonas campestris* pv. *campestris*: Expression in *Escherichia coli* and role in pathogenicity" Mol. Gen. Genet. 210:443–448 (1987).

L. Thorne et al., "Direct utilization of lactose in clarified cheese whey for xanthan gum synthesis by *Xanthomonas campestris*," J. Ind. Microbiol. 3:321–328 (1988).

Keen, et al., "Improved broad-host-range plasmids for DNA cloning in Gram-negative bacteria," Gene 70:191–197 (1988).

Marquet et al., "Improved strains for production of xanthan gum by Fermentation of *Xanthomonas campestris*," J. Ind. Microbiol. 4:55–64 (1989).

Daniels, et al., "Pathogenicity of Xanthomonas and Related Bacteria Towards Plants," Hopwood and Chater Chapter 17:353–371 (1989).

Stripecke et al., "Subcloning and expresison of the O-amylase gene from *Bacillus subtilis* in *Xanthomonas campestris*," Appl. Microbiol. Biotechnol. 31:512–517 (1989).

Pugsley et al., "Genetics of Extracellular Protein Secretion by Gram-negative bacteria," Annu. Rev. Genet. 24:67–90 (1990).

Filloux, et al., "Protein Secretion in Gram-negative bacteria: transport across the outer membrane involves common mechanisms in different bacteria," The EMBO Journal 9:4323–4329 (1990).

Coplin et al., "Molecular Genetics of Extracellular Polysaccharide Biosynthesis in Vascular Phytopathogenic Bacteria," Mol. Plant-Microbe Interact. 3 271–279 (1990).

Groot et al., "Conservation of xcp genes, involved in the two-step protein secretion process, in different Pseudomonas species and other gram-negative bacteria," Mol. Gen. Genet. 229:287–284 (1991).

Dums et al., "Structural characterization of protein secretion genes of the bacterial phytopathogen *Xanthomonas campestris* pathovar *campestris* relatedness to secretion systems of other gram-negative bacteria," Mol. Gen. Genet., 229:357–364 (1991).

Bjorkling et al., "The future impact of industrial lipases," TIBTECH 9:360–363 (1991).

Nien-Tai Hu, et al., "Cloning and Characterization of a Gene Required for the Secretion of Extracellular Enzymes across the Outer Membrane by *Xanthomonas campestris* pv. *campestris*," J. Bacteriol. 124:2679–2687 (1992).

S. Lory, "Determinant of Extracellular Protein Secretion in Gram-Negative Bacteria," J. Bacteriol. 174: 3423–3428 (1992).

Sawczyk et al., Mol. Plant Microbe Interactions 2:249–255 (1989).

Pimena, A. L. et al.; FEMS Microbiol. Lett. 90:11–18 (1991).

Thorne, L. et al: Mutants of *Xanthomonas campestris* Defective in Secretion of Extracellular Enzymes. J. Industrial Microbiol. (1989) 4:135–144.

Tseng, H–C. et al: The Melanin Operon of *Streptomyces antibioticus*: Expression and Use as a Marker in Gram-Negative Bacteria. Gene (1990) 86:123–128.

PROCESS TO OBTAIN EXTRA-CELLULAR RECOMBINANT PRODUCTS USING *XANTHOMONAS CAMPESTRIS* PV *CAMPESTRIS* AS HOST

This application is a continuation, of application Ser. No. 07/929,378, filed Aug. 14, 1992, now abandoned.

BACKGROUND AND BRIEF DESCRIPTION OF THE INVENTION

The development of recombinant DNA technology has permitted the production of foreign products in host organisms which have been transformed with foreign DNA sequences that encode for those products. In general, the DNA coding for the desired polypeptide or protein is introduced into an appropriate site of a cloning vector in order to form a hybrid molecule which is introduced into a compatible cell. A culture of the cell containing the hybrid DNA molecule is used to express the product encoded by the DNA molecule.

The most extended and known use of the bacterium *Xanthomonas campestris* pv *campestris* is the production of xanthan gum, which is a polysaccharide of great commercial value, since this gum in solution is an excellent emulsifier and viscosifier. It is used in the oil industry for enhanced oil recovery. It is also used in agroindustry as well as food and cosmetic industries. The installed world capacity for xanthan gum production is estimated to be 20,000 tons per year. (Yalpani and Sanford. Industrial polysaccharides: Genetic engineering structure/property relations and applications. Elsevier Sciences. Amsterdam, 1989.)

There have been several reports regarding the use of *Xanthomonas campestris* pv *campestris* for xanthan gum production and the optimization of this process; for example, Weber and Horan (U.S. Pat. No. 3,271,267) describe a fermentation to obtain xanthan gum using ground cereal as substrate. On the other hand, there have been some reports about the construction of recombinant *Xanthomonas campestris* strains with the aim of increasing xanthan gum production by overexpressing some of the genes coding for enzymes involved in its biosynthesis. (Thorne et al. 1987. J. Bacteriol. 169: 3593–3600. Harding et al. 1987. J. Bacteriol. 169: 2854–2861).

Genetic engineering technology has also been used to construct *Xanthomonas campestris* strains with a wider capacity to use growth substrates. In this respect a recombinant strain producing $\beta$-galactosidase from transposon Tn 951 (Walsh et al. 1984. Appl. Environ. Microbiol. 47: 253–257), and another expressing $\alpha$-amylase from Bacillus (Stripecke et al. 1989 Appl. Microbiol. Biotechnol. 31: 512–517) have been reported.

The bacterium *Xanthomonas campestris* pv *campestris* has been defined as GRAS (generally regarded as safe) by the U.S. Food and Drug Administration (FDA) agency; therefore products derived from this bacterium would have less restrictions on use in food or pharmaceutical products than the same products expressed by other Gram-negative bacteria such as *Escherichia coli* or *Pseudomonas aeruginosa.*

Research carried out at the Western Utilization Research Laboratory and at Woodward Research Corporation with respect to xanthan gum toxicity as a supplement of rats and dog food, showed that it is resistant to degradation by the digestive system and therefore its use as food additive was approved by FDA.

The most widely used bacterium for the expression of heterologous proteins has been *Escherichia coli.* Several lipases derived from Pseudomonas have been expressed using *E. coil* as host (Othera et al. Japanese patent laid open 60-188072, Kugimiga et al. Japanese patent laid open 62-228279, Wolfare and Winkler. European patent no. 0334462 A1). One of the principal limitations of this host is that enzymes are not secreted so the purification of the recombinant products is more difficult and expensive. *Xanthomonas campestris* pv *campestris* natural isolates produce extracellular enzymes such as proteases and carbohydrases (Daniels, 1989. In Hopwood and Chater eds. Genetics of bacterial diversity. Academic Press.). This characteristic permits the production of extracellular heterologous proteins using *Xanthomonas campestris* pv *capastri* as a host organism for recombinant DNA molecules.

Some Gram-negative bacteria, besides *Xanthomonas campestris,* are able to produce extracellular proteins. These bacteria include Erwinia, Pseudomonas and some Klebsiella species. The protein secretory machinery present in all these Gram-negative bacteria has important similarities (Filloux et al. 1990. EMBO J. 9: 4323–4329).

Some Pseudomonas strains have been used as hosts to express heterologous extracellular lipases derived from different Pseudomonas species (Nakanishi et al. European patent No. 0331 376 A2).

A general characteristic of proteins is that they are stabilized in solution in the presence of viscosifying agents such as glycerol or polyethyleneglycol. In this respect, the activity of a *Pseudomonas aeruginosa* lipase has been reported to be enhanced by the presence of certain polysaccharides such as cellulose or hyaluronate (Jager and Winkler 1983. Fems Microbiol. Lett. 19: 59–63).

The present invention refers to a process of obtaining extracellular recombinant products using *Xanthomonas campestris* pv *campestris* as host, in such a way that the stability of said extracellular recombinant product is enhanced by the presence of xanthan gum. The advantages of the present invention are the following:

The simplicity to purifying the recombinant product and the xanthan gum which are produced extracellularly by *Xanthomonas campestris* pv *campestris.*

The possibility of having less restrictions to introduce in food or pharmaceutical products the recombinant products produced by *Xanthomonas campestris* pv *campestris,* and The enhanced stability of the extracellular recombination heterologous proteins since they are produced in the presence of xanthan gum.

DETAILED DESCRIPTION OF THE INVENTION

The present invention refers to the a process procedure for the production of stabilized extracellular recombinant products by means of the simultaneous production of xanthan gum by a recombinant (transformed) *Xanthomonas campestris* pv *campestris* strain.

The aim of this invention is to provide the conditions to use a recombinant *Xanthomonas campestris* pv *campestris* strain for the production of extracellular recombinant products. This process presents some advantages such as simplicity in the recovery of the recombinant product-xanthan gum mixture; less restrictions in the possible application of the recombinant product in foods or pharmaceuticals, and enhanced product stability because of the presence of xanthan gum.

Another aspect of the invention described herein is to provide the adequate proportion of concentrations of some recombinant products, such as enzymes, and xanthan gum in order to obtain a better enzymatic activity.

The disclosure to follow, about the conditions for the new use of a recombinant *Xanthomonas campestris* pv *campestris* strain for the production of extracellular recombinant products, is made in the understanding that the present description illustrates the method for its use, but that it can suffer slight modifications when it is applied which do not change the essential features of the method, and the resulting procedure will also be included in this invention.

In order that the invention herein described may be more fully understood, the following detailed description is set forth.

In the description the following terms are employed:

Nucleotide—A monomeric unit of DNA or RNA consisting of a sugar moiety (deoxyribose or ribose), a phosphate and a nitrogenous heterocyclic base. The base is linked to the sugar carbon 1, forming a nucleoside. The bases characterize the nucleotides. The four DNA bases are adenine (A), guanine (G), cytosine (C) and thymine (T). The four RNA bases are A, G, C and uracil (U).

DNA sequence—A linear array of nucleotides connected one to the other by phosphodiester bonds between the 3′ and 5′ carbons of adjacent deoxyriboses.

Polypeptide—or protein A linear array of amino acids connected one to the other by peptide bonds between the α-amino and carboxyl groups of adjacent amino acids.

Gene—A DNA sequence which encodes through a messenger RNA (mRNA), an amino acid sequence characteristic of a specific polypeptide.

Transcription—The cellular process of producing mRNA from a gene or DNA sequence.

Translation—The cellular process of producing a polypeptide from mRNA. Expression—The cellular process of producing a polypeptide from a DNA sequence or gene. It involves transcription and translation.

Plasmid—A double stranded DNA sequence able to replicate independently from the chromosome. When a plasmid is present in an unicellular organism, the characteristics of that organism may be changed or transformed as a result of the genes encoded in the plasmid, for example 1 a plasmid containing the gene for ampicillin resistance transforms a cell which is sensitive to this antibiotic into one which is resistant to it. A host cell transformed by a plasmid is called a "transformant".

Plasmid vehicle—A plasmid which can be maintained in a specific host cell, and which is characterized by one or a small number of endonuclease recognition sites at which the plasmid can be cut without losing its abilities to be maintained in the cell.

Recombinant plasmid—A molecule consisting of a segment of a genome (the entire DNA of a cell or virus) and a plasmid vehicle which have been joined end to end outside a living cell and which can transform a specific host cell.

Expression control sequence—A DNA sequence which controls and regulates the expression of a gene when it is operatively linked to that gene.

Inducer—A compound which promotes the expression of a gene by means of its indirect interaction with an expression control sequence.

Recombinant product—A cell product which is, at least in part, encoded by a recombinant plasmid.

The present invention relates to the procedure to produce extracellular recombinant products by a *Xanthomonas campestris* pv *campestris* strain containing a recombinant plasmid. This plasmid contains an expression control sequence which permits the production of the extracellular recombinant product in the presence of a specific inducer.

In the present invention it is also shown that a transformant strain of *Xanthomonas campestris* pv *campestris* secretes into the culture medium an extracellular protein encoded by a Pseudomonas gene. The recombinant product represented by this Pseudomonas protein, is not secreted by *Escherichia coil.*

It is important to note that although the present invention is described as utilizing as recombinant products proteins encoded by genes derived from Pseudomonas, the method of this invention is applicable to a wide variety of extracellular recombinant products derived from other Gram-negative bacteria such as Erwinia or Klebsiella, or even to products derived from unrelated microorganisms such as Gram-positive bacteria, yeast or fungi if they are expressed and secreted by *Xanthomonas campestris* pv *campestris.*

The utilization of the recombinant (transformed) *Xanthomonas campestris* pv *campestris* strain comprises the following steps: a) A preculture of the bacteria in rich medium, b) Separation of the bacteria and their rinsing with sterile saline solution, c) Growth of the bacteria on a specific growth medium with the addition of an inducer which promotes the expression of the extracellular recombinant product, and d) Separation of the bacteria from the culture supernatant which contains the mixture of the recombinant product and xanthan gum.

In order to understand better the present invention, the following examples are set forth. These examples are for purpose of illustration only, and are not to be construed as limiting the scope of the invention in any manner.

EXAMPLE 1

The following example is illustrative of the method for producing an extracellular recombinant product, which in this case is specifically a lipase, by a transformant strain of *Xanthomonas campestris* pv *campestris.*

The recombinant plasmid used to tranform *Xanthomonas campestris* pv *campestris* is called pBP13, it was constructed from an RSF1010 derivative which contains an expression control sequence regulated by isopropylthio-β-D-galactoside; (IPTG) or lactose. A *Pseudomonas aeruginosa* gene coding for an extracellular lipase was inserted into this plasmid vehicle.

A *Xanthomonas campestris* pv *campestris* strain containing plasmid pBP13 was grown during 24 hours on a rich medium (PYG); this medium in % (g/100 ml): 0.5 peptone, 0.3 yeast extract, and 0.2 glucose. The cells were harvested by centrifugation and rinsed twice with 0.85% (w/v) sterile saline solution. The washed cells were inoculated to PYG medium containing 1.0% -(w/v) lactose, at a proportion of 1:40. The flasks were incubated at a temperature between 29° C. and 32° C., and shaken at 200rpm, for a period of 24 to 30 hours. The culture supernatant is separated by centrifugation at 10,000 rpm for 15 min. The supernatant is the product which contains a suspension of xanthan gum and the lipase derived from *Pseudomonas aeruginosa*. The product is conserved refrigerated at 4° C.

When 125 mi. Erlenmeyer flasks with 20 ml. of medium were used, the activity of the lipase detected was between 200-500 units/mi. When 250 ml. baffled Erlenmeyer flasks with 20 ml. of medium were used, no lipase activity was detected.

Method to determine lipase activity. The lipase activity present in the xanthan gum-enzyme mixture was determined by the following procedure: 4 g of tributyltin are emulsified in 400 ml of 0.05M Tris buffer pH 8.5 by agitation in a blender for 5 min. 6ml of the tributyltin emulsion are heated to 55° C. and 4 ml of the supernatant are added, once this mixture reaches 55° C., the pH is maintained at 8.5 by the addition of 0.05M NaOH and the volume added and time are recorded. The amount of NaOH used to maintain the pH corresponds to the amount of fatty acids generated by the lipase activity. One unit of lipase corresponds to one nM of fatty acid released per minute.

EXAMPLE 2

This example is illustrative of the effect on lipase production by a strain of *Xanthomonas campestris* pv *campestris* containing plasmid pBP13 of the culture medium and the type of inducer.

A *Xanthomonas campestris* pv *campestris* strain containing plasmid pBP13 was grown in similar conditions as example 1, with the difference that medium M9 was used; this medium contains in % (g/100 ml): 0.6 Na$_2$HPO$_4$, 0.3 KH$_2$PO$_4$, 0.05 NaCl, 0.1 NH$_4$CL, 0.05 MgSO$_4$ and 0.0011 CaCl$_2$ adjusted to; pH 7.4; and IPTG was used as inducer in a concentration or 1 to 5 mM. the lipase activity of the culture supernatant varied between 180 and 270 units/ml in these conditions.

EXAMPLE 4

This example is illustrative of the xanthan gum production by a *Xanthomonas campestris* pv *campestris* strain containing plasmid pBP13.

When the *Xanthomonas campestris* pv *campestris* strain containing plasmid pBP13 is grown for 48 hrs. at, 29° C. on a 250 ml baffled Erlenmeyer flask with 100 ml of medium XGP it produces between 9 and 12 g/l of xanthan gum. XGP contains in g/l, sucrose 24, (NH$_4$)$_2$SO$_4$1 MgSO$_4$ 0.23, citric acid 1.3, KH$_2$PO$_4$3.9, CaCO$_3$ 0.0027, H$_3$BO$_4$0.0048, ZnO 0.0072, FeCl$_3$0.0014 ph7.

I claim:

1. A process to obtain lipase using *Xanthomonas campestris* pv *campestris* as a host organism, comprising growing a *Xanthomonas campestris* pv *campestris* strain transformed with a recombinant plasmid containing a DNA sequence encoding lipase from a species of Pseudomonas, thereby producing lipase, and recovering the resulting culture supernatant containing lipase.

2. The process of claim 1 wherein the production of lipase is controlled by a specific inducer which is included in a growth medium where the transformed *Xanthomonas campestris* pv *campestris* is cultivated.

3. A process to obtain lipase from *Xanthomonas campestris* pv *campestris*, comprising the following steps:
   (a) constructing a recombinant plasmid by inserting DNA comprising a DNA sequence encoding lipase from a species of Pseudomonas into a plasmid vehicle so that the DNA is under the regulation of a functional expression control sequence which is part of the plasmid vehicle and which is capable of being induced by a specific inducer;
   (b) transforming a *Xanthomonas campestris* pv *campestris* host with the recombinant plasmid comprising the DNA sequence encoding lipase;
   (c) culturing the transformed host on a growth medium which contains the specific inducer of the expression of the DNA sequence encoding lipase, and which permits xanthan gum production; and
   (d) recovering the resulting culture supernatant containing lipase and xanthan gum.

4. A process to obtain lipase using *Xanthomonas campestris* pv *campestris* as a host organism, comprising growing a *Xanthomonas campestris* pv *campstris* strain transformed with a recombinant plasid containing DNA encoding lipase from *Pseudomonas aeruginosa, Pseudomonas cepacia*, or *Pseudomonas glumae*, thereby producing lipase, and recovering the resulting culture supernatant containing lipase.

5. The process of claim 4 wherein the production of lipase is controlled by a specific inducer which is included in a growth medium where the transformed *Xanathomonas campestris* pv *campestris* is cultivated.

6. The process to obtain lipase from *Xanthomonas campestris* pv *campestris*, comprising the following steps:
   (a) constructing a recombination plasmid by inserting DNA encoding lipase from *Pseudomonas aerguinosa, Pseudomonas cepacia*, or *Pseudomonas glumae* into a plasmid vehicle so that the DNA is under the regulation of functional expression control sequence which is part of the plasmid vehile and which is capable of being induced by a specific inducer;
   (b) transforming a *Xanthomonas campestris* pv *campestris* host with the recombinant plasmid comprising the DNA encoding lipase,
   (c) culturing the transformed host on a growth medium which contains the specific inducer of the expression of the DNA encoding lipase, and which permits xanthan gum production; and
   (d) recovering the resulting culture supernatant containing lipase and xanthan gum.

7. The process of claim 6, 4, or 5, wherein the species is *Pseudomonas aeruginosa* or *Pseudomonas cepacia*.

8. The process of claim 7, wherein the species is *Pseudomonas aeruginosa*.

* * * * *

UNITED STATES PATENT AND TRADEMARK OFFICE
CERTIFICATE OF CORRECTION

PATENT NO. : 5,443,980
DATED : August 22, 1995
INVENTOR(S) : Soberón-Chávez

It is certified that error appears in the above-indentified patent and that said Letters Patent is hereby corrected as shown below:

Title page, item [54], and column 1, line 1, change "EXTRA-CELLULAR" to

--EXTRACELLULAR--.

Inventor, title Page, line 2, change

"Cristobalcuernavaca" to --Cristobal, Cuernavaca, Morelos--.

Abstract, title Page, line 2, change "capestris"

to --campestris--.

Claim 1, column 5, lines 57 and 58, Italicize

"*Pseudomonas*".

Claim 3, column 6, line 9, Italicize "*Pseudomonas*".

Claim 4, column 6, line 25, change "campstris"

to --campestris--; column 6, line 26, change "plasid"

to --plasmid--.

Claim 5, column 6, line 34, change "Xanathomonas" to

--Xanthomonas--.

UNITED STATES PATENT AND TRADEMARK OFFICE
CERTIFICATE OF CORRECTION

PATENT NO. : 5,443,980
DATED : August 22, 1995
INVENTOR(S) : Soberón-Chávez

It is certified that error appears in the above-indentified patent and that said Letters Patent is hereby corrected as shown below:

Claim 6, column 6, line 35, change "The" to --A--; column 6, line 38, change "recombination" to --recombinant--; column 6, lines 39-40, change "aerguinosa" to --aeruginosa--; column 6, line 43, change "vehile" to --vehicle--.

Claim 7, column 6, line 55, change "6, 4, or 5" to --4, 5, or 6--.

Signed and Sealed this

Twenty-third Day of January, 1996

Attest:

BRUCE LEHMAN

*Attesting Officer*            *Commissioner of Patents and Trademarks*

UNITED STATES PATENT AND TRADEMARK OFFICE
CERTIFICATE OF CORRECTION

PATENT NO. : 5,443,980
DATED : August 22, 1995
INVENTOR(S) : Soberon-Chavez

It is certified that error appears in the above-indentified patent and that said Letters Patent is hereby corrected as shown below:

On the title page, item [73], change "Univeridad" to --Universidad--.

Signed and Sealed this

Second Day of April, 1996

Attest:

BRUCE LEHMAN

*Attesting Officer*     *Commissioner of Patents and Trademarks*